(12) United States Patent
Baxley

(10) Patent No.: US 9,226,718 B1
(45) Date of Patent: Jan. 5, 2016

(54) IMAGE RECEPTOR SUPPORT DEVICE

(71) Applicant: Alicia Baxley, Tucson, AZ (US)

(72) Inventor: Alicia Baxley, Tucson, AZ (US)

( * ) Notice: Subject to any disclaimer, the term of this patent is extended or adjusted under 35 U.S.C. 154(b) by 147 days.

(21) Appl. No.: 13/960,577

(22) Filed: Aug. 6, 2013

(51) Int. Cl.
*A61B 6/04* (2006.01)

(52) U.S. Cl.
CPC .......................................... *A61B 6/04* (2013.01)

(58) Field of Classification Search
CPC ................................ A61B 6/502; A61B 6/0414
USPC ............................................................ 378/37
See application file for complete search history.

(56) References Cited

U.S. PATENT DOCUMENTS

| | | | |
|---|---|---|---|
| 4,943,986 A * | 7/1990 | Barbarisi | 378/37 |
| 4,962,515 A * | 10/1990 | Kopans | 378/37 |
| 5,081,657 A * | 1/1992 | Klawitter et al. | 378/37 |
| 6,146,377 A | 11/2000 | Lee et al. | |
| 6,577,702 B1 * | 6/2003 | Lebovic et al. | 378/37 |
| 6,997,608 B2 | 2/2006 | Sisto et al. | |
| D559,985 S | 1/2008 | Dzierlatka | |
| 2004/0010193 A1 | 1/2004 | Entrekin et al. | |
| 2004/0220479 A1 | 11/2004 | Wake | |
| 2005/0008117 A1 | 1/2005 | Livingston | |
| 2006/0050844 A1 * | 3/2006 | Galkin | 378/37 |
| 2009/0135997 A1 | 5/2009 | Defreitas et al. | |
| 2009/0259128 A1 | 10/2009 | Stribling | |
| 2010/0049093 A1 | 2/2010 | Galkin | |
| 2010/0204580 A1 | 8/2010 | Zhang et al. | |
| 2012/0033786 A1 | 2/2012 | Zinreich Shafer et al. | |
| 2012/0114096 A1 | 5/2012 | Lebovic et al. | |
| 2012/0119100 A1 | 5/2012 | Muraoka | |
| 2013/0129039 A1 | 5/2013 | Defreitas et al. | |

* cited by examiner

*Primary Examiner* — Hoon Song
(74) *Attorney, Agent, or Firm* — Invention To Patent Services; Alex Hobson

(57) ABSTRACT

An image receptor support device having a more comfortable patient engagement side is described. The patient engagement side has a concave central portion, a rounded left portion and rounded right portion. A patient may more comfortably position their body against the interceptor support device and more effectively position a body part over and image receptor. An image receptor support device may be configured for mammograms, for example. An image receptor support device may comprise a comfort material such as a foam or elastomer that is compressible and not cold to the touch. A concave central portion may be centrally located between the left and right side or offset. In addition, the bottom surface of the patient engagement side may be recessed from the top surface. A patient engagement side may be configured to be a detachable interface with an existing image receptor support device.

19 Claims, 8 Drawing Sheets

IMAGE RECEPTOR SUPPORT DEVICE

BACKGROUND OF THE INVENTION

1. Field of the Invention

The present invention relates to an image receptor support device and particularly those used for mammogram systems.

2. Background

Mammograms have become routine diagnostic requiring the placement of a woman's breasts over an image receptor. X-rays pass through the breast tissue to create an image for examination. An image receptor support device, sometimes referred to as a Bucky plate, provides the support and patient interface surface for conducting this procedure. An image receptor support device typically comprises a substantially x-ray transparent material that allows the x-rays to pass through to the image receptor. An image receptor may be a physical sheet or a digital receptor. AN image receptor may be configured to slide into an image support device. Many women put off or completely refrain from scheduling mammograms as they find the procedure to be very uncomfortable. Image receptor support devices are not configured with a woman's comfort in mind. They are typically a rectangular plate having relatively sharp edges. Women must press hard against the support device for proper positioning of the breast, and this rectangular shaped image receptor support sometimes causes bruising along the patient's rib cage and/or abdomen. In addition, the sharp edges of the rectangular shaped image receptor support can be very uncomfortable as it presses into the patients skin. Furthermore, the image receptor support device is typically cold to the touch making the procedure more uncomfortable. Patients confined to a wheelchair often find it particularly difficult to position themselves properly against an image receptor support device.

SUMMARY OF THE INVENTION

The invention is directed to an image receptor support device that is configured with a patient engagement side having a concave central portion, a rounded left portion and rounded right portion. The image receptor support device, of the present invention, allows a woman to more easily and comfortably position their body to achieve proper placement of their breast over an image receptor. The curved central portion enables more complete placement of the breast over the image receptor portion of the machine without causing excess pressure against the patient. In some embodiments, an image receptor support device comprises a top surface and a bottom surface, wherein the bottom surface, along the patient engagement side, is recessed from the top surface. This recessed bottom surface further reduces unnecessary pressure against the patient. An image receptor support device or detachable interface to an image receptor support device may allow better positioning of a particular body part over and image receptor and therefore result in a better diagnosis of the patient's condition.

The concave central portion of the patient engagement side may comprise a contour having a radius of any suitable dimension including, but not limited to a radius of about 10 cm or more, about 12 cm or more, about 20 cm or more, about 25 cm or more, about 38 cm or more and any range between and including the radius values provided. The concave center portion may be centrally located between the left and right sides of the image receptor support device or offset from a central location. The concave central portion may have any suitable concave shape including bowl shaped and irregular shaped, for example. An irregular shaped patient engagement side may further improve positioning of the breast over the image receptor while being comfortable to the patient.

The rounded left and rounded right portions comprise a contour having a radius of any suitable dimension including, but not limited, about 5 cm or more, about 15 cm or more, about 20 cm or more, about 25 cm or more, about 38 cm or more and any range between and including the radius values provided. The rounded left and rounded right portions may extend to the sides of the image receptor support device or extend beyond the sides, wherein the corners of the image receptor support device along the patient engagement side are rounded.

An image receptor support device, as described herein, comprises a substantially x-ray transparent material and in some cases a specific imaging portion consisting essentially of an x-ray transparent material. In some embodiments, an image receptor support device comprises an imaging port whereby an imaging receptor may be inserted therein. In other embodiments, the image receptor support device is configured for use with a digital image receptor and may be configured for positioning over the digital image receptor.

An image receptor support device may have any suitable dimensions and may be sized according to the body part to be examined. In an exemplary embodiment, an image receptor support device has a depth extending from a patient engagement side to the imaging device and a width extending from the left side to the right side. An image receptor support device may have any suitable depth or width including, but not limited to, about 10 cm or more, about 15 cm or more, about 18 cm or more, about 20 cm or more, about 24 cm or more, about 30 cm or more, about 36 cm or more, and any combination or any range between and including the dimensions provided. For example, an image receptor support device may have a width of 24 cm and a depth of 18 cm, or a width of 30 cm and a depth of 24 cm.

In an exemplary embodiment, at least a portion of the bottom surface along the patient engagement side is recessed from the top surface. This recess allows the patient to more comfortably press up against the imagery receptor support device whereby their rib cage and/or abdomen are provided additional room. The bottom surface may have any suitable recess depth including, but not limited to, about 5 mm or more, about 12 mm or more, about 25 mm or more, about 50 mm or more and any range between and including the recess depth values provided. The top surface of the patient engagement side of the image receptor support device may be rounded and have any suitable radius. A patient engagement side may have a radius including about 12 mm or more, about 25 mm or more about 10 cm or more, about 15 cm or more and any range between and including the radius values provided. Any portion of the patient engagement side may be recessed including substantially the entire patient engagement side.

The image receptor support device, as described herein, may comprise a comfort material along at least a portion of the patient engagement side. A comfort material is any material that has a shore A hardness of less than about 100 and may include foams, felts, fabrics, elastomeric material, composite materials and any combination thereof. In an exemplary embodiment, a patient engagement side comprises a foam that is not cold to the touch like a metal. In an exemplary embodiment, a comfort material is detachable from the image receptor support device, as described herein.

In an exemplary embodiment, an image receptor support device comprises a detachable patient interface. For example, a patient interface may be configured to have an interference fit over the edge of an existing image receptor support device to create the patient engagement side. In another embodiment, a patient interface may be configured to be attached through the use of a fastener including a screw, clip, adhesive, hook and loop fastener material and the like.

In an exemplary embodiment, an image receptor support device comprises a heating element configured along the patient engagement side. A heating element may be configured in a detachable patient interface. The heating element may be used to increase the temperature of the image receptor support device particularly along the patient engagement side for a patient's comfort. A heating element may be powered in any suitable way including with batteries, electrical wiring or an electrical plug. Batteries may be configured within the image receptor support device along the patient engagement side, for example.

The image receptor support device, of the present invention, may be used in conjunction with any x-ray machine. In an exemplary embodiment, it is configured for use with a mammogram machine. However, it is to be understood that the concepts described herein may be utilized for image receptor support devices utilized in any suitable application having a patient interface side.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention and, together with the description, serve to explain the principles of the invention.

DETAILED DESCRIPTION OF THE ILLUSTRATED EMBODIMENTS

Figure 1:
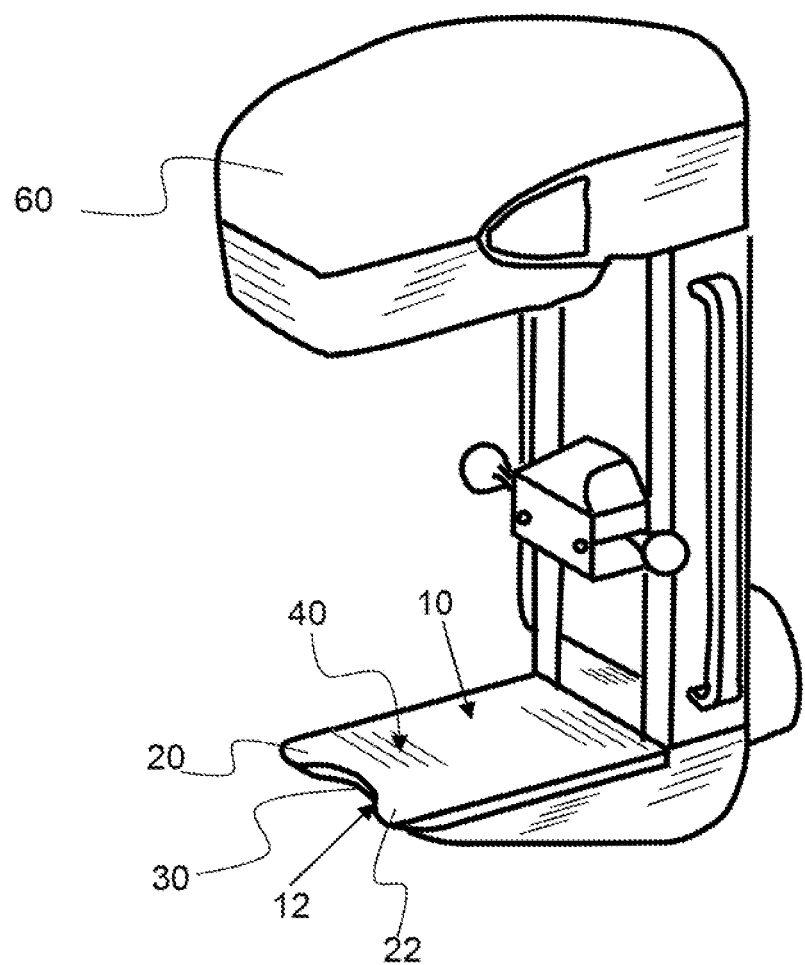

FIG. 1 shows a perspective view of a mammogram device comprising an exemplary image receptor support device.

Figure 2:
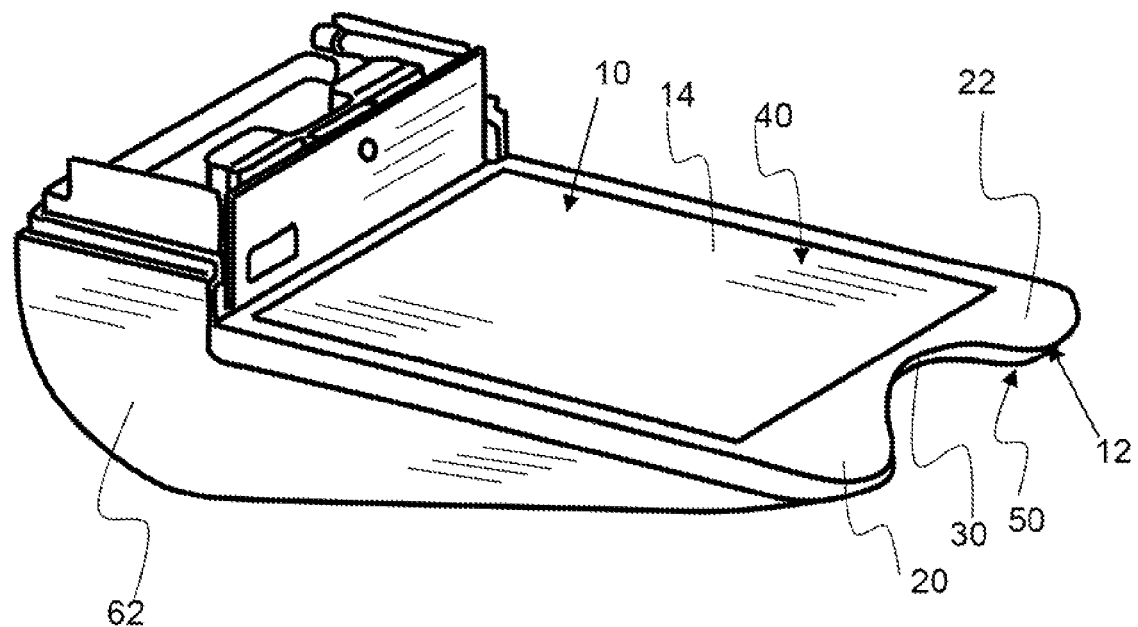

FIG. 2 shows a perspective view of an exemplary image receptor support device configured on an x-ray machine.

Figure 3:
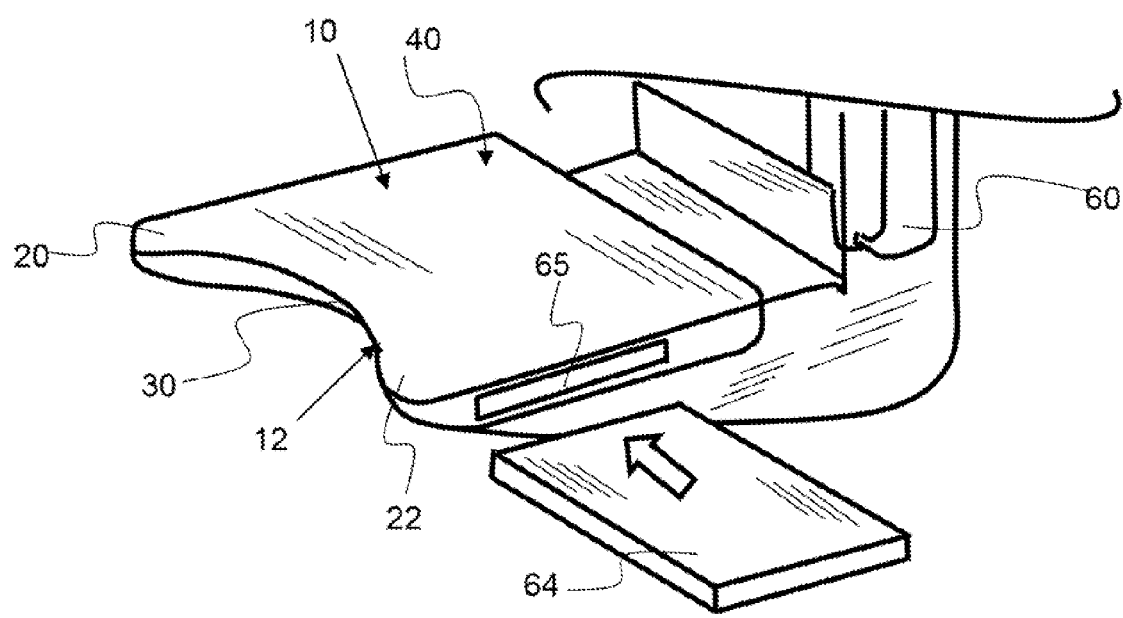

FIG. 3 shows a perspective view of an exemplary image receptor support device having an image receptor port.

Figure 4:
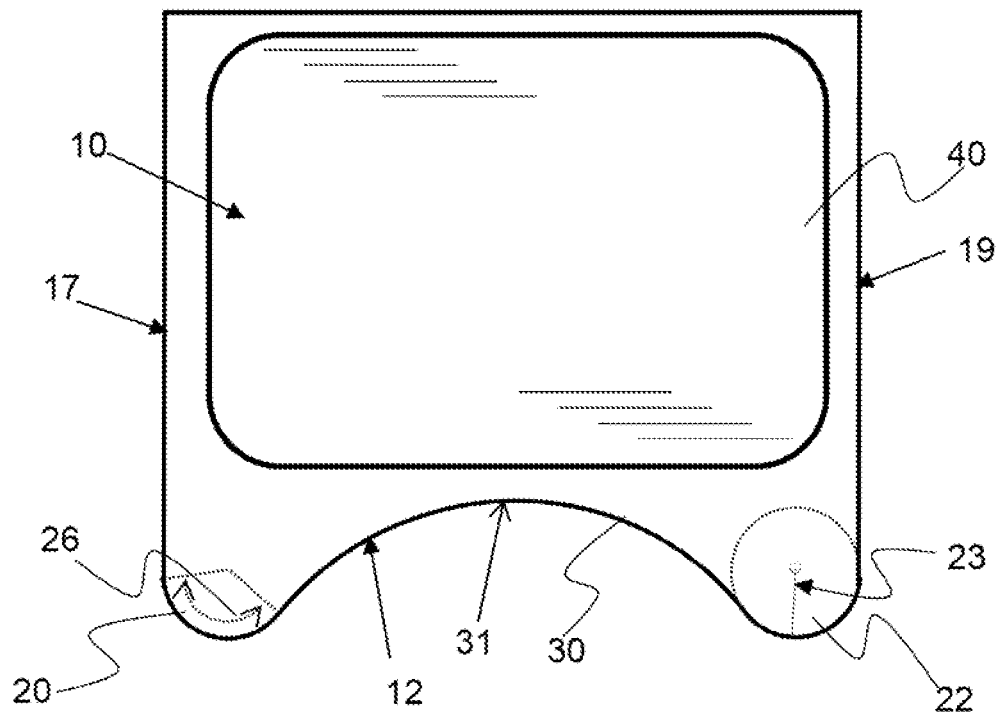

FIG. 4 shows a top-down view of an exemplary image receptor support device having a contoured patient engagement side.

Figure 5:
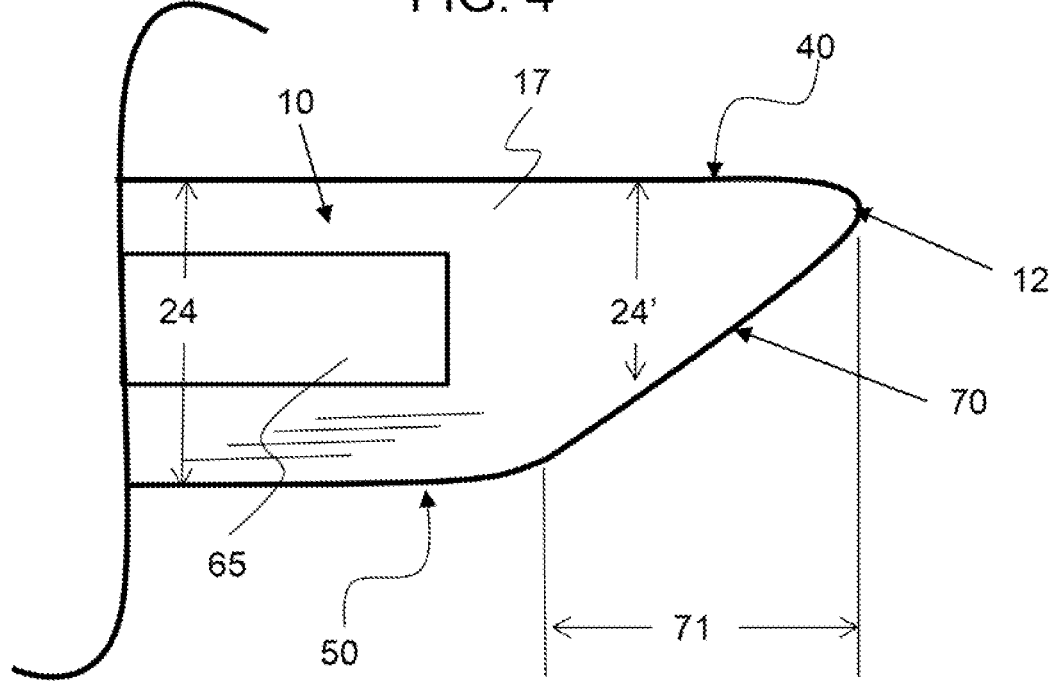

FIG. 5 shows a side view of an exemplary image receptor support device having a bottom surface recessed from a top surface.

Figure 6:
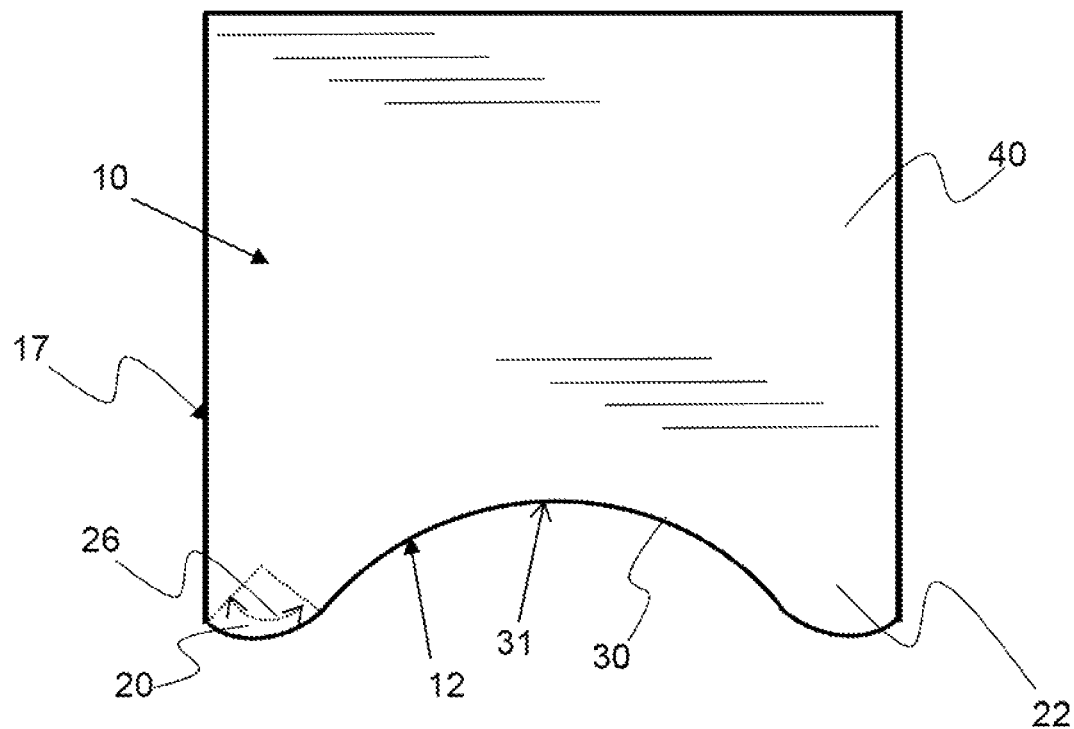

FIG. 6 shows a top-down view of an exemplary image receptor support device as described herein.

Figure 7:
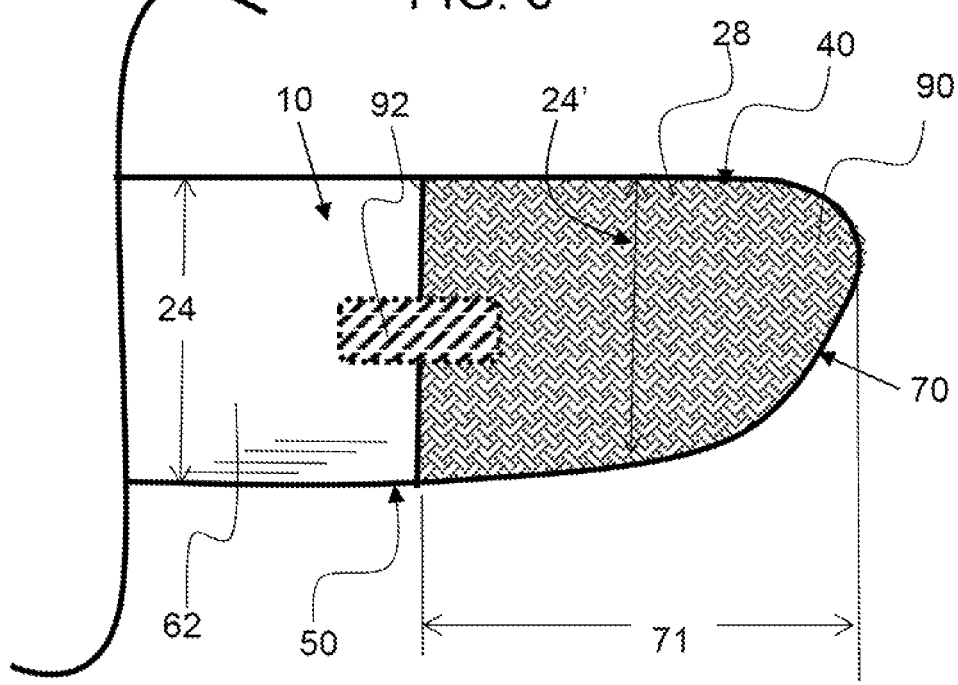

FIG. 7 shows a side cross-sectional view of an exemplary image receptor support device having a detachable patient interface.

Figure 8:
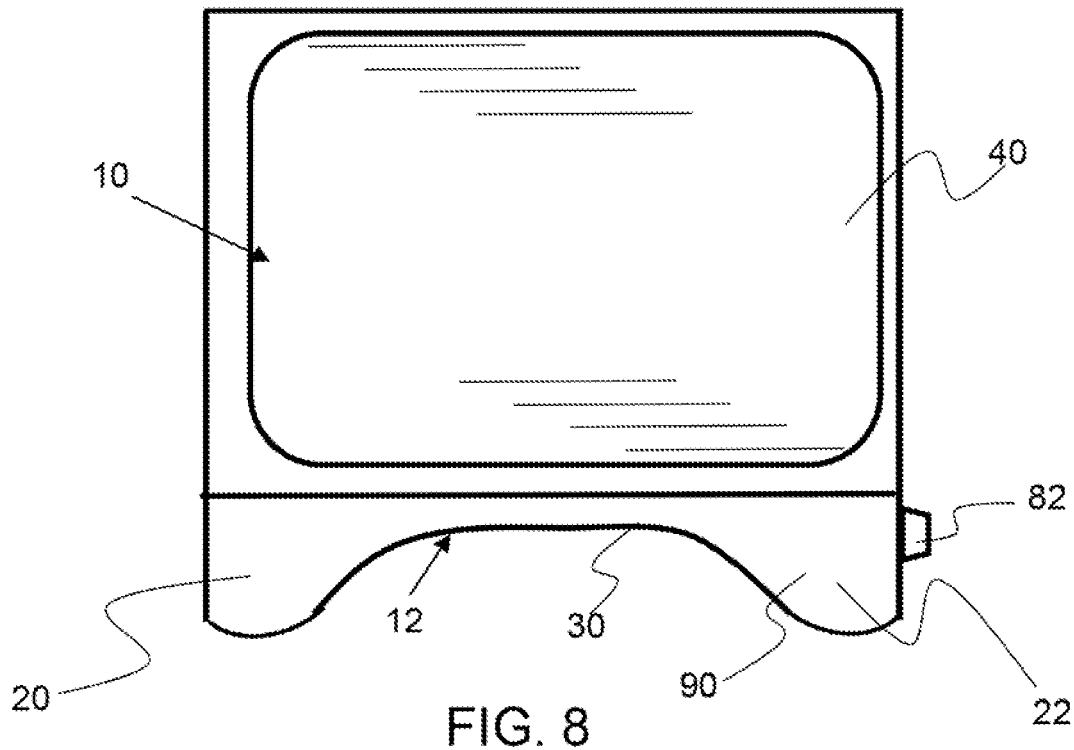

FIG. 8 shows a top-down view of an exemplary image receptor support device.)

Figure 9:
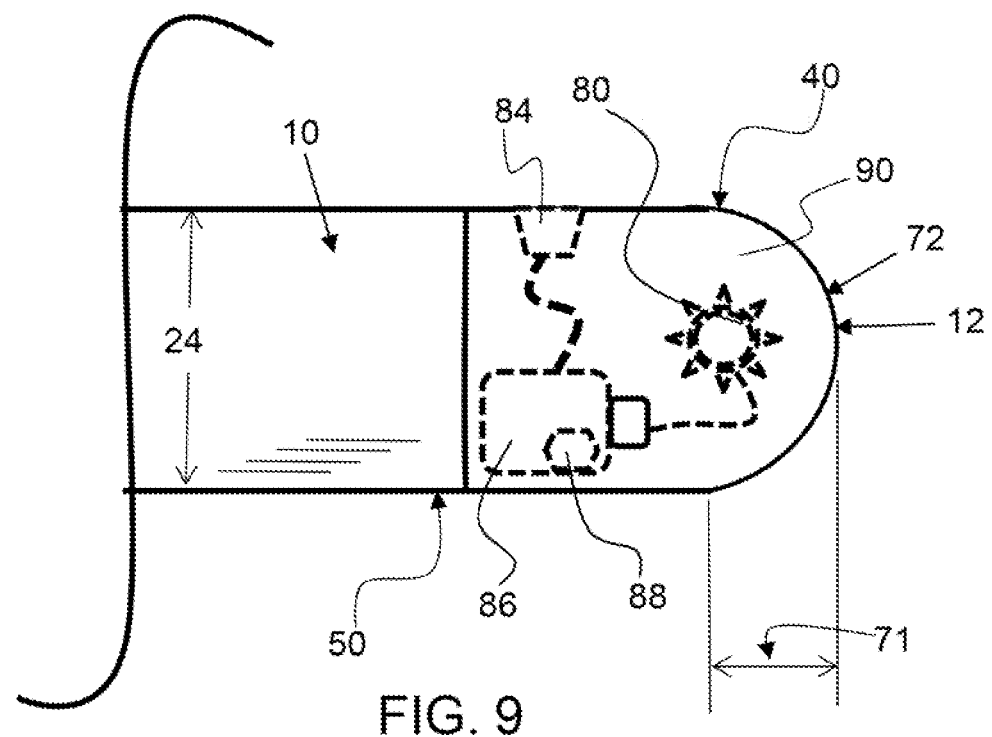

FIG. 9 shows a side view of an exemplary image receptor support device comprising a heating element along the patient engagement side.

Figure 10:
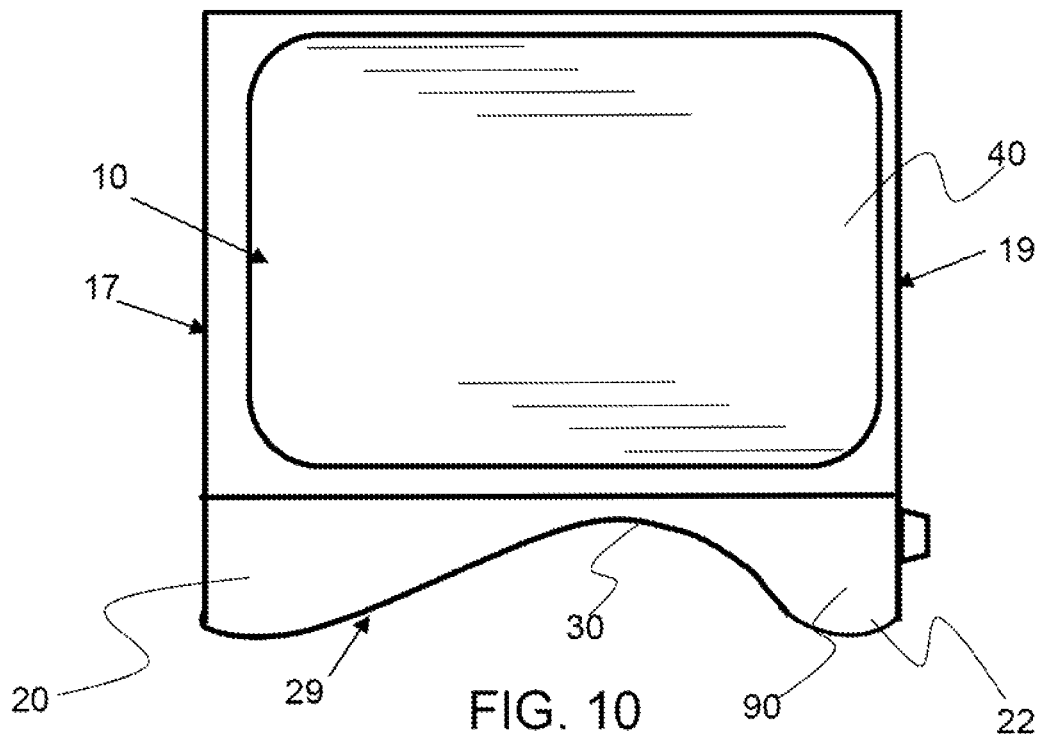

FIG. 10 shows a top-down view of an exemplary image receptor support device have an irregularly shaped patient engagement side.

Figure 11:
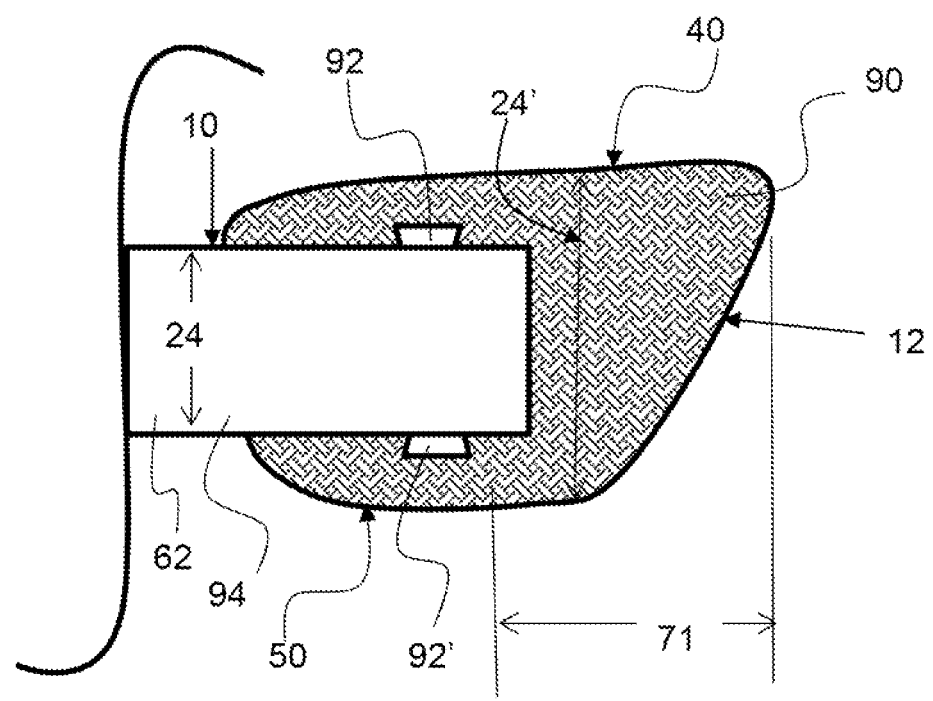

FIG. 11 shows a side view of a detachable patient interface comprising a comfort material.

Figure 12:
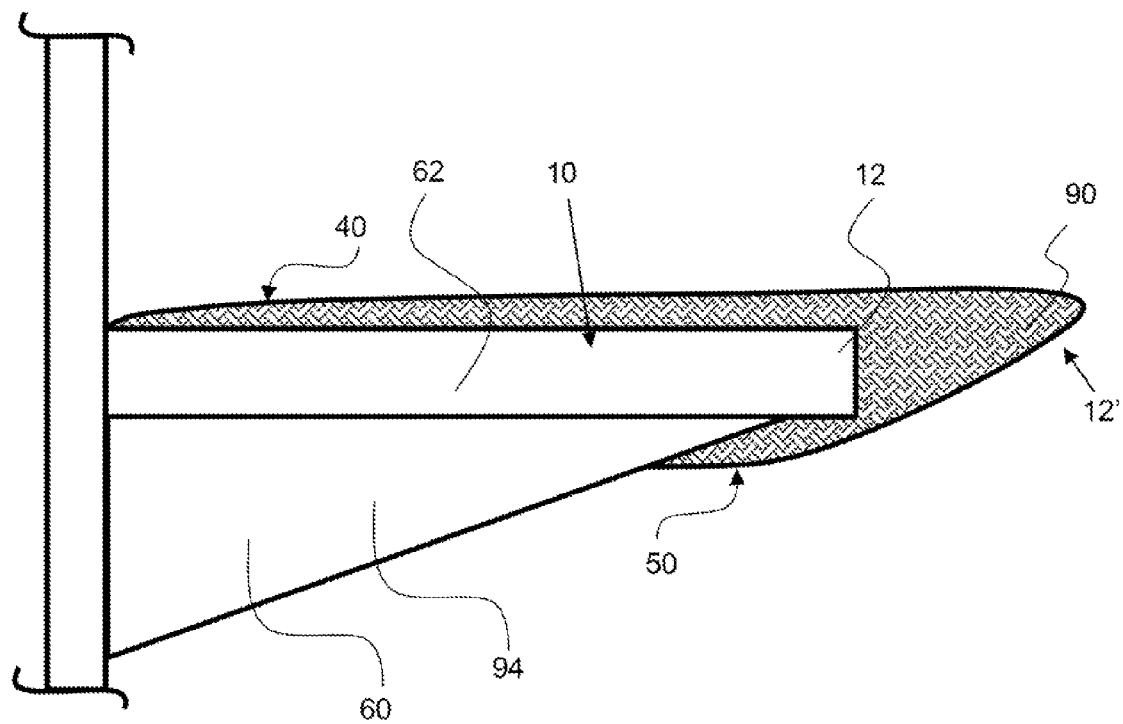

FIG. 12 shows a side view of a detachable patient interface comprising a comfort material that extends substantially over and image receptor portion.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and illustrated in the accompanying figures. The embodiments described are only for purposes of illustrating the present invention and should not be interpreted as limiting the scope of the invention. Other embodiments of the invention, and certain modifications, combinations, and improvements of the described embodiments, will occur to those skilled in the art and all such alternate embodiments, combinations, modifications, improvements are within the scope of the present invention.

As shown in FIG. 1, a mammogram device 60 comprises an exemplary image receptor support device 10. The patient engagement side 12 comprises a concave central portion 30, a rounded left portion 20 and a rounded right portion 22.

As shown in FIG. 2, an exemplary image receptor support device 10 is configured on an x-ray machine 62. The top surface 40 comprises an imaging portion 14 and a contoured patient engagement side 12. As described, the imaging portion may consists essentially of a substantially x-ray transparent material and the rest of the image receptor support device may be made out of a different material that may not substantially x-ray transparent. The bottom surface 50 is recessed from the top surface 40. The corners of the image receptor support device along the patient engagement side are rounded.

As shown in FIG. 3, an exemplary image receptor support device 10 has an image receptor port 65 configured to receive an image receptor 64. As described herein, any suitable type of image receptor may be used in conjunction with the image receptor support device. In some cases, a digital image receptor is configured under the image receptor support device.

As shown in FIG. 4, an exemplary image receptor support device 10 has a contoured patient engagement side 12. The concave central portion 30 is centrally located between the left and right sides 17, 19 respectively. The rounded left portion 20 extends an arc of approximately 120°, as indicated by the dashed arc line. The left and right corners along the patient engagement side are rounded. The radii of curvatures 23 of the rounded left and right portions is indicated by the dashed circle over the rounded right portion 22.

As shown in FIG. 5, an exemplary image receptor support device 10 has a bottom surface 50 recessed from a top surface 40. The recessed side 70 has a recess depth 71 as indicated. The recess depth 71 is the distance from the front of the patient engagement side to where the thickness 24 of the image receptor support device is substantially uniform. The thickness 24 of the image receptor support device is reduced as shown by thickness 24' along the recessed side. An image receptor port 65 is shown configured along the left side 17 of the image receptor support device 10.

As shown in FIG. 6, an exemplary image receptor support device 10 comprises rounded left and right portions having an arc 26 as indicated. The arc 26 extends approximately 90 degrees from the inflection point with the concave central portion 30 to the left side 17.

As shown in FIG. 7, an exemplary image receptor support device 10 has a detachable patient interface 90. The detachable patient interface consists essentially of a comfort material and is attached to the image receptor portion by a fastener 92. Any suitable fastener may be used to attach a patient interface to an image receptor support device. The recess depth 71 of the recess side 70 extends substantially to image receptor portion 62.

As shown in FIG. 8, an exemplary image receptor support device 10 comprises a detachable interface 90. The detachable interface is configured to be attached to form the patient engagement side 12 and comprises a concave central portion 30, a rounded left portion 20 and rounded right portion 22. An on/off switch 82 is configured on the detachable interface 94 to activate a heating element (not shown) within the detachable interface.

As shown in FIG. 9, an exemplary image receptor support device comprises a heating element 80 along the detachable interface 90. A battery 86 is configured within the detachably interface to power the heating element. A sensor 84, such as a contact sensor, may be configured to automatically turn on the heater or increase the heat output as a function of a patient interfacing with the device. A controller 88 may be configured to control output from the battery to the heater and may turn off the heater if the sensor does not detect a patient interface for a predetermined period of time. The controller may also turn on and off the heater, or increase or decrease the power output of the heater to maintain a desired temperature. A temperature sensor may be configured on or within an image receptor support device or detachable interface to provide temperature input to the controller. A controller may maintain a temperature within a desired and preset range to ensure a comfortable temperature and to prevent the image receptor support device or detachable interface from overheating. It is to be understood that a heating element may be configured along the patient engagement side 12 of any image receptor supply device as described herein. The patient engagement side 12 shown in FIG. 9 comprises a radius of curvature 72 and a relatively small recess depth 71.

As shown in FIG. 10, an exemplary image receptor support device 10 has an irregularly shaped patient engagement side 12. The concave central portion 30 is not centered between the left and right side, 17 and 19 respectively, of the image receptor support device 18. This configuration may allow the patient to position their body against the image receptor support device in a more comfortable manner. The detachable interface 90 may be detached and reattach with the left side becoming the right side to allow the patient to comfortably position the other breast on the image receptor support device 10.

As shown in FIG. 11, an exemplary detachable interface 90 comprises a comfort material that is configured to extend over a portion of the image receptor portion 62 of the image receptor support device 10. A fastener 92 on the top and bottom of the image receptor portion 62 are configured to temporarily retain the detachable interface. The top surface 40 and bottom surface 50 of the detachable interface extend beyond the surface of the image receptor portion 62. The image receptor portion 62 is configured at least partially within an opening or slot within the detachable interface 90.

As show in FIG. 12, a detachable patient interface 90 comprising a comfort material 28 that extends substantially over the entire depth of the image receptor support device 62. In this embodiment, fasteners may not be necessary to retain the detachable patient interface 90 to the image receptor support device 10. The detachable patient interface may comprise an elastomeric comfort material that has a high coefficient of friction and effectively stays in place when configured around the patient engagement side 12 of an image receptor support device. A new patient engagement side 1Z is created by the attached detachable patient interface. The detachable patient interface 90 has a slot configured therein for receiving the patient engagement side 12 of the image receptor support device 62.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A mammogram image receptor support device comprising:
    an image receptor portion;
    a detachable patient interface that is configured to detachably attach to and extend only along a patient interface side of the mammogram image receptor support device;
        wherein the detachable patient interface does not extent over the image receptor portion;
        wherein the detachable patient interface is configured for contact with a patient during use; and
        wherein the detachable patient ace comprises:
            a rounded left portion;
            a rounded right portion;
            a concave central portion;
    a top surface;
    the bottom surface,
    whereby said mammogram image receptor support device comprises a substantially x-ray transparent material.

2. The mammogram image receptor support device of claim 1, further comprising an imaging receptor port.

3. The mammogram image receptor support device of claim 1, wherein the concave central portion is centrally located along the patient engagement side between a left and a right side of the image receptor support device.

4. The mammogram image receptor support device of claim 1, wherein the concave central portion comprises an arc having a radius of at least about 20 cm.

5. The mammogram image receptor support device of claim 1, whereby at least a portion of the bottom surface along the patient engagement side is recessed from the top surface.

6. The mammogram image receptor support device of claim 1, whereby the bottom surface along the patient engagement side is recessed at least about 12 mm from the top surface.

7. The mammogram image receptor support device of claim 1, whereby substantially the entire bottom surface along the patient engagement side is recessed from the top surface.

8. The mammogram image receptor support device of claim 1, whereby all edges of the patient engagement side are rounded and have a radius of at least 12 mm.

9. The mammogram image receptor support device of claim 1, wherein the detachable patient interface comprises a comfort material.

10. The mammogram image receptor support device of claim 1, wherein the detachable patient interface comprises a heating element.

11. The mammogram image receptor support device of claim 10, wherein the heating element extends substantially along the entire patient engagement side.

12. A mammogram image receptor support device comprising:
   an image receptor portion;
   a detachable patient interface that is configured to detachably attach to and extend only along a patient interface side of the mammogram image receptor support device;
      wherein the detachable patient interface does not extent over the image receptor portion;
      wherein the detachable patient interface is configured for contact with a patient during use; and
   wherein the detachable patient interface comprises
      a rounded left portion;
      a rounded right portion;
      a concave central portion;
      a comfort material having a share A hardness of less than 100;
   a top surface;
   the bottom surface, and
   an imaging portion consisting of an x-ray transparent material;
whereby at least a portion of said bottom surface along said patient engagement side is recessed from said top surface.

13. The mammogram image receptor support device of claim 12, wherein the comfort material consists of a foam.

14. The mammogram image receptor support device of claim 12, further comprising a heating element configured within the detachable patient interface.

15. The mammogram age receptor support device of claim 12, wherein the patient engagement side consists of the detachable patient interface.

16. A detachable patient interface for an image receptor support device configured to detachably attach to and extend only along a patient interface side of a mammogram image receptor support device;
   wherein the detachable patient interface does not extent over an image receptor portion of the mammogram image receptor support device;
   wherein the detachable patient interface is configured for contact with a patient during use; and
   wherein the detachable patient interface a comprises:
      a rounded left portion;
      a rounded right portion;
      a concave central portion;
      iv. a comfort material;
   a top surface.

17. The detachable patient interface of claim 16, wherein the concave central portion is centrally located along the patient engagement side.

18. The detachable patient interface of claim 16, wherein the a comfort material has a shore A hardness of less than 100.

19. The detachable patient interface of claim 16, further comprising a heating element configured within the detachable patient interface.

* * * * *